United States Patent
Driscoll

(10) Patent No.: US 9,423,386 B2
(45) Date of Patent: Aug. 23, 2016

(54) METHOD FOR ION DETECTION

(71) Applicant: John N. Driscoll, Centerville, MA (US)

(72) Inventor: John N. Driscoll, Centerville, MA (US)

( * ) Notice: Subject to any disclaimer, the term of this patent is extended or adjusted under 35 U.S.C. 154(b) by 0 days.

(21) Appl. No.: 14/672,132

(22) Filed: Mar. 28, 2015

(65) Prior Publication Data

US 2015/0301008 A1    Oct. 22, 2015

Related U.S. Application Data

(60) Provisional application No. 61/975,903, filed on Apr. 6, 2014.

(51) Int. Cl.

| | |
|---|---|
| *G01N 27/62* | (2006.01) |
| *G01N 30/88* | (2006.01) |
| *G01N 33/20* | (2006.01) |
| *G01N 33/00* | (2006.01) |
| *G01N 30/06* | (2006.01) |
| *G01N 30/96* | (2006.01) |

(Continued)

(52) U.S. Cl.
CPC .......... *G01N 33/0013* (2013.01); *G01N 30/06* (2013.01); *G01N 30/88* (2013.01); *G01N 33/0045* (2013.01); *G01N 27/628* (2013.01); *G01N 30/96* (2013.01); *G01N 2030/009* (2013.01); *G01N 2030/067* (2013.01); *G01N 2030/085* (2013.01); *G01N 2030/143* (2013.01); *G01N 2030/642* (2013.01); *G01N 2030/8868* (2013.01); *G01N 2030/8872* (2013.01); *G01N 2033/0019* (2013.01)

(58) Field of Classification Search
CPC .................. G01N 33/0045; G01N 2033/0019; G01N 27/628

USPC ........................................................... 436/81
See application file for complete search history.

(56) References Cited

U.S. PATENT DOCUMENTS

| | | | | |
|---|---|---|---|---|
| 3,859,807 A | * | 1/1975 | Benedict | .................. B01D 8/00 |
| | | | | 62/55.5 |
| 4,013,913 A | | 3/1977 | Driscoll et al. | |

(Continued)

OTHER PUBLICATIONS

McCleskey et al., "Cation-Exchange Separation of Interfering Metals From Acid Mine Waters for Accurate Determination of Total Arsenic and Arsenic(III) by Hydride Generation-Atomic Absorption Spectrometry" (2001) 43rd Rocky Mountain Conference on Analytical Chemistry, Denver, CO.*

(Continued)

*Primary Examiner* — Paul Hyun
(74) *Attorney, Agent, or Firm* — Robert R. Deleault, Esq.; Mesmer & Deleault, PLLC

(57) ABSTRACT

A method for detecting a chemical species includes providing in a vessel an acidic sample containing an ionic chemical species to be measured where a substrate of the species to be formed is ionizable by radiant energy provided by a photo-ionization detector in detector system and a headspace above the acidic sample, adding a preselected reducing agent to the aqueous sample and forming an ionizable chemical gas species in the aqueous sample where the ionizable chemical gas species evolves out of the aqueous sample and into the headspace forming a gas sample, moving the gas sample containing the ionizable chemical gas species from the headspace of the vessel out of the vessel and through a precolumn, and moving the gas sample containing the ionizable chemical gas species from the precolumn into one of (1) a detector system or (2) an oxygen-retaining column before the detector system.

18 Claims, 16 Drawing Sheets

(51) Int. Cl.
   *G01N 30/00* (2006.01)
   *G01N 30/08* (2006.01)
   *G01N 30/14* (2006.01)
   *G01N 30/64* (2006.01)

(56) References Cited

U.S. PATENT DOCUMENTS

| | | | |
|---|---|---|---|
| 4,413,185 A | 11/1983 | Leveson et al. | |
| 7,507,273 B1 * | 3/2009 | Massie | B01D 53/04 203/19 |
| 2002/0100366 A1 | 8/2002 | Watanabe et al. | |

OTHER PUBLICATIONS

Tanaka, Tatsuhiko et al., "Simultaneous Determination of Phosphorus, Sulfur and Arsenic in Steel by Hydride Generation and Gas Chromatography," Analytical Sciences, Feb. 1996, pp. 77-80.

Holak, Walter, "Gas-Sampling Technique for Arsenic Determination by Atomic Absorption Spectrophotometry," Analytical Chemistry, 1969, pp. 1712-1713.

Mergemeier, Steffen et al., "Application of the photoionization detector for single determinations of hydride forming elements," Fresenius' Journal of Analytical Chemistry, 1994, vol. 350, pp. 659-661.

Vien, Steve H. et al., "Ultrasensitive, Simultaneous Determination of Arsenic, Selenium, Tin, and Antimony in Aqueous Solution by Hydride Generation Gas Chromatography with Photoionization Detection," Analytical Chemistry, 1988, vol. 60, pp. 465-472.

Yamamoto, Masahiro et al., "Selective determination of trace arsenic and antimony species in natural waters by gas chromatography with photoionization detector," Applied Organometallic Chemistry, 1992, vol. 6, pp. 351-356.

Cutter, G, A., "Speciation of selenium and arsenic in natural waters and sediments, vol. 1, Selenium speciation, Final report," 1986, abstract only.

Filippino, K. C. et al., "Photochemical Effects on Arsenic Speciation in Surface Waters Monograph Title: EOS, Transactions, Americal Geophysical Union EOS Trans. Am. Geophys. Union," 2001, vol. 82, abstract only.

Driscoll, Jack N. et al., "Photoionization (PID) and GC-PID method for the measurement of arsenic in food and juice," Abstracts of Papers American Chemical Society, Aug. 19, 2012, vol. 244, abstract only.

Puanngam, Mahitti et al., "A cold plasma dielectric barrier discharge atomic emission detector for atmospheric mercury," Talanta, 2010, vol. 81, pp. 1109-1115.

Cutter, Lynda S. et al., "Simultaneous Determination of Inorganic Arsenic and Antimony Species in Natural Waters Using Selective Hydride Generation with Gas Chromatography/Photoinization Detection," Analytical Chemistry, 1991, vol. 63, pp. 1138-1142.

European Search Report from the European Patent Office, in co-pending European Patent Appl. No. 15 000 961.1, mail date Dec. 7, 2015.

* cited by examiner

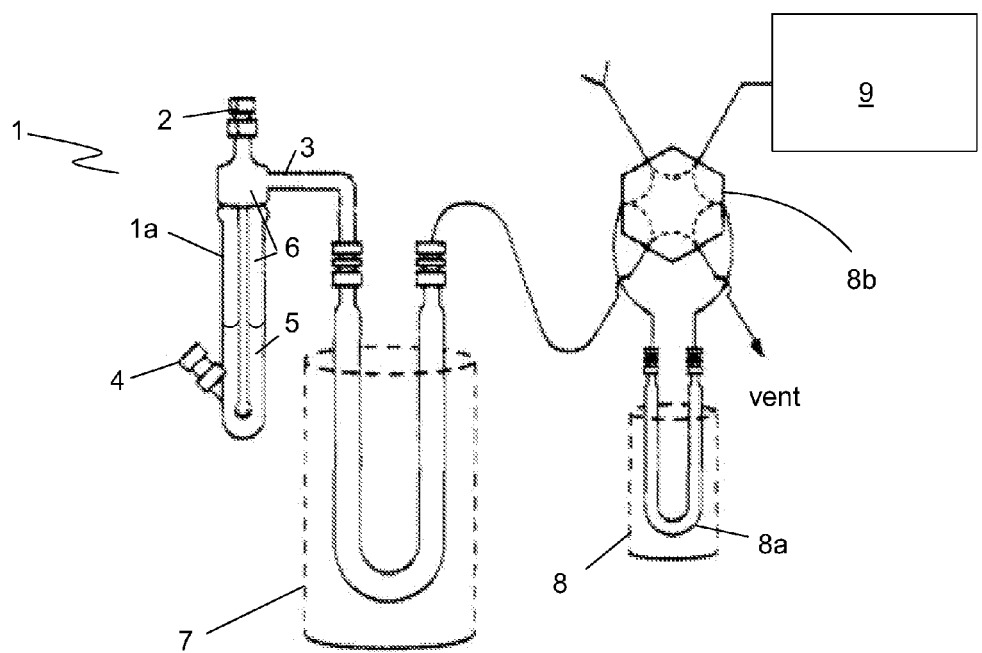
Fig. 21 - *Prior Art*

METHOD FOR ION DETECTION

This application claims the benefit of U.S. Provisional Patent Application No. 61/975,903, filed Apr. 6, 2014.

BACKGROUND OF THE INVENTION

1. Field of the Invention

The present invention relates generally to the detection of species ionized by radiant energy. Particularly, the present invention relates to a method of detecting hydrides or mercury ionized by radiant energy using photoionization.

2. Description of the Prior Art

Photoionization as a scientific concept has been known for some time. The first application of photoionization detection was as a gas chromatography (GC) ion detector for hydrocarbons. In a photoionization detector high-energy photons, typically in the ultraviolet (far UV) range, break molecules into positively charged ions. As compounds elute from the GC's column they are bombarded by high-energy photons and are ionized when molecules absorb high energy UV light. UV light excites the molecules, resulting in temporary loss of electrons in the molecules and the formation of positively charged ions. The gas becomes electrically charged and the ions produce an electric current, which is the signal output of the detector. The greater the concentration of the component, the more ions are produced, and the greater the current.

More particularly, the photoionization process is initiated when a photon of sufficient energy (from a short wavelength UV lamp) is absorbed by a molecule. This results in the creation of a positive ion and an electron as shown below:

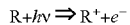

$$R + h\nu \Rightarrow R^+ + e^-$$

where:

R=an ionizable species hv=a photon with sufficient energy to ionize species R

In the ion chamber, the ions ($R^+$) formed by absorption of the UV photons are collected by applying a positive potential (100-200 V) to the accelerating electrode and measuring the current at the collection electrode. The current produced is proportional to the concentration over a very wide range. Once the collection electrode is shielded from the UV to reduce the background current, and the geometry is axial, the field strength is given by:

$$E = V/(2.3r \text{ Log } a/b)$$

where

V is the applied voltage between the collector of radius a and the accelerating electrode of radius b, and E is the electric field at any point in distance r from the center of the accelerating electrode.

As a result, the field increases rapidly as r→b. The most effective ion chamber design is where there is a coaxial configuration. These design characteristics provide a PID with the lowest background, best possible sensitivity and widest dynamic range.

Hydride generation is a procedure commonly used for sensitivity enhancement in a variety of instrumental methods for measuring trace levels of As, Se, Sb, Sn, Ge, Te, and Bi (and sometimes Pb) in aqueous solutions and wet-ashed solid samples. A hydride is a compound in which one or more hydrogen atoms have reducing, or basic properties. In hydrides, hydrogen is bonded to a more electropositive element such as a metal. When metal hydride forming compounds in solution are treated with a reducing agent, the hydride $MH_3$ (g) is formed.

For atomic spectral analysis, the hydride technique typically results in several orders of magnitude improvement in concentration sensitivity over conventional nebulizer sample introduction. The two instrumental methods most commonly coupled to hydride preconcentration are atomic absorption and plasma emission spectrometry. When either of these two detectors are used with the most recent commercially available, state-of-the-art, automated, continuous-flow hydride generators, solution-phase concentration detection limits in the range of 0.2-0.4 ppb As, Se, and Sn can be routinely achieved. Generally liquid nitrogen was used to preconcentrate the sample.

The photoionization approach to hydride detection replaces atomic absorption and plasma emission detectors. A photoionization detector (PID) and a liquid nitrogen cold trap (i.e. a concentrator) provides several orders of magnitude of sensitivity improvement over the best existing continuous-flow hydride generation atomic absorption and plasma emission systems for As, Se, and Sn determination (without suffering any significant selenium hydride loss).

SUMMARY OF THE INVENTION

It is an object of the present invention to provide a method of detecting metals, non-metals or metalloids using hydride generation and a photoionization detector.

The present invention achieves these and other objectives by providing a method for detecting ionized species that includes, in one embodiment, hydride generation, and in another embodiment, an ionizable gas of an element, and directly measuring a hydride species or the ionizable gas of an element, respectively, using a photoionization detector without using a liquid nitrogen trap.

In one embodiment of the present invention, the method includes providing providing in a vessel an acidic sample containing an ionic chemical species to be measured where a substrate of the species to be formed is ionizable by radiant energy provided by a photoionization detector in the detector system and where the vessel has a headspace above the acidic sample, adding a preselected reducing agent to the aqueous sample and forming an ionizable chemical gas species in the aqueous sample whereby the ionizable chemical gas species evolves out of the aqueous sample and into the headspace forming a gas sample, moving the gas sample containing the ionizable chemical gas species from the headspace of the vessel out of the vessel and through a precolumn, and moving the gas sample containing the ionizable chemical gas species from the precolumn into one of (1) a photoionization detector or a gas chromatograph having a photoionization detector when the headspace is purged with nitrogen gas prior to performing the adding step, or, when the headspace contained oxygen when the adding step is performed (2) an oxygen-retaining column before moving the gas sample into a photoionization detector or a gas chromatograph having a photoionization detector. The precolumn retains water and other organics of the gas sample in the precolumn while passing the gas sample containing the ionizable chemical gas species through the precolumn.

In another embodiment of the present invention, the method includes selecting a column that receives the gas sample from the group consisting of a packed column, a PLOT column, or a capillary column before being ionized by radiant energy using PID.

In in further embodiment of the present invention, the method includes selecting one of a capillary column that is a thick film capillary column or selecting a PLOT column packed with a porous polymer.

In still another embodiment of the present invention, the method includes selecting an ionic sample having one or more of a metal, nonmetal or metalloid that forms a hydride.

In yet another embodiment of the present invention, the method includes selecting a sample having one or more ionic species selected from the group consisting of arsenic, antimony, cadmium, lead, iron, chromium, selenium, tellurium, bismuth, tin, mercury, hydrogen selenide, and hydrogen telluride.

In another embodiment of the present invention, the method includes selecting an aqueous sample having an ionic species wherein a substrate of the ionic species has an ionization potential in the range of 8-12 eV.

In another embodiment, the method includes selecting sodium borohydride or Sn—HCl as the reducing agent.

In another embodiment, the method further includes adding an oxidizing agent to the ionic sample for metals such as Pb or Fe and others. In a further embodiment the oxidizing agent is hydrogen peroxide.

In still another embodiment of the present invention, the method includes passing a predefined quantity of aqueous ionic sample containing the ionic species through a cation exchange column and desorbing the ionic species from the cation exchange column with smaller predefined quantity of a salt solution before placing the sample in the vessel.

In yet another embodiment, the method includes passing the gas sample through a concentrator column to accumulate the ionizable chemical gas species in the concentrator column before moving the gas sample into the photoionization detector or a gas chromatograph having a photoionization detector. After a predefined time accumulating the ionizable chemical gas species in the concentrator column, the column is then quickly heated to a predefined temperature to release the ionizable chemical gas species. The the released ionizable chemical gas species is then passed into the photoionization detector or a gas chromatograph having a photoionization detector.

In another embodiment, the method includes selecting a concentrator column that contains (1) activated charcoal when the ionizable chemical gas species is an ionizable gas hydride substrate of the chemical species or (2) gold film when the ionizable chemical gas species is mercury. When the concentrator column contains activate charcoal, the heating step includes heating to a temperature of 150° C. in about 1 to about 2 minutes. When the concentrator column contains gold film, the heating step includes heating to 500° C. in about 30 seconds.

In one embodiment, the method includes selecting a vessel that is a sparger.

In another embodiment, the method includes selecting a vessel that is a VOA vial with a septum and no headspace above the acidic sample and removing a predefined quantity of the sample from the vessel through the septum creating the headspace.

In another embodiment, the method further includes stirring the aqueous sample when adding the preselected reducing agent and continuing the stirring until eluting of the gas sample is complete.

In still another embodiment, there is a method for detecting mercury in air by a photoionization detector system. The method includes passing a substantial quantity of air through a concentrator column containing gold film whereby a gold-mercury amalgam is formed, purging the concentrator with nitrogen gas for a predefined period of time to remove oxygen and other organics from the concentrator quickly heating the gold film concentrator to a substantial temperature (500° C.) to decompose the gold-mercury amalgam forming mercury gas, and injecting the mercury gas into a photoionization detector system. The concentrator column is heated to 500° C. in about 30 seconds.

Another aspect of the present invention is the concentrator for mercury whether used for air or aqueous sampling. The concentrator has a quartz body with a concentrator inlet connected to a first body end, a concentrator outlet connected transversely to the quartz body, a heater end connected to a second body end, and a stainless steel rod coated with a gold film disposed within the quartz body and extending out of the heater end a predefined distance.

The advantages of the present invention is that it is easy to use, does not require a high level of training, and has a low capital cost.

BRIEF DESCRIPTION OF THE DRAWINGS

FIG. 21 is a schematic illustration showing the apparatus of the prior art.

DETAILED DESCRIPTION

Definitions

A "precolumn" means a six inch (15.24 cm) length of a column packed with a porous polymer or a short thick film capillary column. An example of an acceptable porous polymer is the porous polymer sold under the trademark HayeSep® N.

An "oxygen-retaining column" means a packed column or a PLOT column or a capillary column of sufficient length where the retention time of oxygen in the column is longer than the retention time for an ionizable chemical gas species.

An "ionizable chemical gas species" means an ionizable gas hydride substrate of the chemical species or an ionizable gas of a chemical element of the chemical species.

Conventional wisdom of those of ordinary skill in the art is that the PID detector is used for hydrocarbon detection. Other techniques are typically used for transition metals, post-transition metals and metalloids. The most popular techniques that are typically used include hydride generation with atomic absorption spectrometry (HGAAS) or atomic fluorescence spectrometry (HGAFS), graphite furnace atomization with AAS detection (GFAAS) to improve sensitivity, inductively coupled plasma with optical emission spectrometry (ICP-OES), inductively coupled plasma with mass spectrometry (ICP-MS) with ultrasonic nebulization, anodic stripping voltammetry (ASV), and spectrophotometry.

Both atomic absorption and atomic fluorescence spectrometry are sensitive, single element-specific techniques with known and controllable interferences. However, AAS and AFS are almost always coupled to the method of hydride generation where arsenic (As(III), As(V)) is reduced to the As(III) oxidation state, producing the volatile gas arsine ($AsH_3$) that is then either preconcentrated using liquid nitrogen or swept directly into the detector. The inductively coupled plasma techniques offer the possibility of examining many contaminants since they are multi-element techniques, again with known and controllable interferences (e.g., As is monoisotopic so isobaric interferences are common). Anodic stripping voltammetry is a useful technique for samples containing only free dissolved arsenic. The spectrophotometric method, which is also a single element technique, has the advantage of being relatively inexpensive in terms of equipment.

In the early 1980's, an automatic GC (gas chromatograph) with a PID was introduced that would detect low parts-per-billion levels of $AsH_3$ (5 ppb) and $PH_3$ (2 ppb). This technique remains one of the most sensitive methods for the detection of $AsH_3$. Photoionization (PID) techniques for arsenic in water have been well described. More recently, the PID detector has been used for the detection of arsenic in water using a hydride generator down to 1 part per billion. When a GC/PID method is used, the sample needs to be concentrated because the amount of sample injected into the GC is much smaller than the direct PID method.

Figure 17:
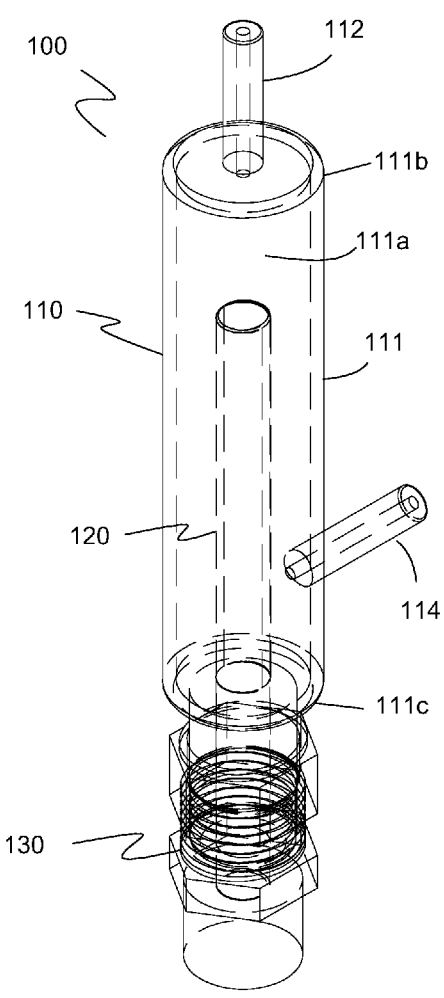
FIG. 17 is a perspective view of one embodiment of a concentrator and heater attachment for measuring mercury using a PID analyzer system.

The typical GC/PID method involves collecting the $AsH_3$ in a liquid nitrogen trap (glass U-tube packed with silanized glass wool), and then the collected $AsH_3$ is removed from the liquid nitrogen trap by applying heat to re-volatize the arsine, which is then swept into the GC with a packed column. The flow of nitrogen gas is continues throughout the GC/PID method. FIG. 17 illustrates a schematic of the GC/PID method with the liquid nitrogen trap. The method includes adding sample to a sparger 1, which is a vessel 1a having a typical capacity of 70-100 cc and that has an inlet 2 and an outlet 3 and an injection port 4 (septum) to inject a liquid sample into vessel 1a. A liquid sample 5, typically in the amount of 40 cc, is placed in the vessel, 1 cc of a reducing agent such as 4% sodium borahydride is added to the liquid sample. The metal salt ($MO_3^{-3}$) (i.e. the ionic species) is reduced to a metal hydride ($MH_2$) gas (i.e. the ionizable substrate of the species). The liquid sample 5 is continuously purged with nitrogen gas ($N_2$) through inlet 2 to agitate the liquid sample 5 and to remove $MH_3$ gas from the liquid sample 5 and the head space 6 and elute it to a water vapor trap 7 having a temperature of about −50 degrees centigrade before eluting to a liquid nitrogen trap 8 containing a U-tube 8a where the $MH_3$ gas is cooled and trapped. After this step, the trapped metal hydride is heated rapidly and desorbed into an Atomic Absorption spectrometer or a GC 9. A six-way valve 8b is typically used to facilitate sample handling prior to injection into the AA or GC 9.

It is known that oxygen will quench the PID response and is best represented by the following equations:

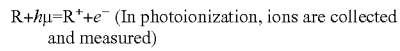
R+$h\mu$=R$^+$+e$^-$ (In photoionization, ions are collected and measured)

$O_2$+e$^-$=$O_2^-$

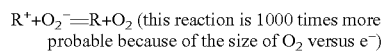
R$^+$+$O_2^-$=R+$O_2$ (this reaction is 1000 times more probable because of the size of $O_2$ versus e$^-$)

Quenching by water is due to the same mechanism as described above for $O_2$. In addition, water absorbs photons strongly at 120 nm thereby reducing the number of photons available for photoionization.

Thus, water must also be removed from the nitrogen stream used in the prior art, which is typically done with a separate cold trap 7 as shown in FIG. 17 or a drying agent (not shown) prior to the nitrogen stream containing the metal hydride entering the liquid nitrogen trap.

Like the prior art, the present invention includes hydride generation by adding an acid solution (e.g., 0.6 M HCl) to the aqueous sample, then adding the reducing agent (e.g., $NaBH_4$). The present invention differs from the prior art techniques in the method of generating and preparing the ionic species and/or a substrate of the ionic species for injection into a PID or a GC/PID. In one embodiment, a non-continuous purge of nitrogen into the vessel is used. In another embodiment, a continuous purge of nitrogen into the vessel may be used. Most notably, the present invention differs from the prior art techniques by the absence of (i.e. without the use of) a liquid nitrogen trap. In some embodiments, the present invention differs from the prior art techniques by the absence of a heated desorbing step. In other words, no liquid nitrogen trap is used in the method of the present invention, which is required in the prior art to concentrate the metal hydride flowing in the continuous stream of nitrogen gas eluting from the vessel that must then be rapidly heated to re-volatize the metal hydride before injecting into the PID or GC/PID. Also, the present invention does not require a separate concentrator except for certain low level ppt measurements of particular species.

The reaction vessel used in the present invention for hydride generation may be either a sparger or a VOA vial, which is discussed later. The sparger is a vessel having about an 80 cc capacity with an inlet, an outlet and a septum for the addition of a reducing agent and, optionally, an oxidizing agent. A stirring mechanism, such as, for example, a magnetic stirrer, is optionally and preferably used to agitate the solution and to more quickly drive the $MH_3$ gas into the headspace of the vessel. Because oxygen will quench the PID response, nitrogen gas is used to purge the sample and the headspace of oxygen and prepare the sample for the generation of the $MH_3$ gas especially when low parts-per-billion levels need to be measured. The nitrogen purge is typically performed for several minutes and then stopped. After a predefined time of performing the nitrogen purge of the vessel containing the aqueous sample having the species of interest, a reducing agent and, optionally, an oxidizing agent is added to the acidic aqueous sample depending on the species in the aqueous sample. For a reducing agent such as sodium borohydride ($NaBH_4$), the amount of $NaBH_4$ added to the aqueous sample is in the range of about 4%. The higher end being required for low ppb levels of the species to be measured in the aqueous sample. The inclusion of the oxidizing agent is provided in some cases such as, for example, iron or lead, to oxidize the sample to $Fe^{+3}$ from $Fe^{+2}$ or $Pb^{+4}$ from $Pb^{+2}$. An example of an oxidizing agent is hydrogen peroxide ($H_2O_2$). Although the $MH_x$ gas species would naturally release from the aqueous sample over time, magnetic stirring is preferably used to agitate the sample containing the reducing agent and/or the oxidizing agent and to quickly release the $MH_x$ gas from the aqueous sample. The nitrogen purge is then stopped for a predefined time before eluting the gas sample from the sparger. The gas sample may be eluted manually or by an automatic injection system.

In the embodiment incorporating a stirring mechanism where the nitrogen purge is stopped, the stirring continues after the nitrogen purge is stopped. To allow the buildup of $MH_x$ gas in the headspace of the sparger, a predefined time (depending on the levels to be detected) after the nitrogen purge is stopped passes before a predefined quantity (preferably about 1 cc) of the $MH_x$ gas is eluted from the headspace of the sparger to or injected into the PID detector or the GC with the photoionization detector. For levels greater than 50 ppb, the predefined time is about 2-6 minutes. The increase in sensitivity from a 2 minute sample to a 5 minute sample can be from 3-5 times. For levels lower than 50 ppb, the predefined time is about 10-12 minutes. At high levels of water vapor, the signal is severely quenched, however, when a GC is used, the GC separates the metal-related signal from the water vapor signal. It is noted that the nitrogen purge may be continuous provided that other mechanisms as described herein are used to concentrate the metal of the $MH_3$, particularly when low ppb or lower levels are to be detected.

To improve the quality of the data output from the photoionization detector, the $MH_3$ gas may optionally be passed through (1) an oxygen-retaining column before being injected into the PID or the GC/PID or (2) a precolumn before being injected into the PID or the GC/PID or (3) both an oxygen-retaining column and a precolumn before being injected into the PID or the GC/PID, as the case may be depending on an initial content of a headspace in the reaction vessel. The column is one of a packed column, a porous layer open tubular (PLOT) column or a capillary column. The packed column is preferably one that is a 1/8" (0.32 cm) column, six feet (182.9 cm) long and packed with porous polymer sold under the trademark Tenax® GS or Chromsorb® or Hayesep® or Poropak®. For a packed column, nitrogen purging for several minutes may be necessary to remove $O_2$ at low part-per-billion (ppb) concentrations. The PLOT column is packed with a porous polymer. The most preferred column to be optionally used is the capillary column. The preferred capillary column is a thick film capillary column since it not only can be used for aqueous samples but is better for analysis of foods and juices that contain significant levels of organic compounds. An example of a capillary column would be a 30 meter×0.53 mm with various liquid phases. The "thick film" is typically 0.32 mm thick with 3-8 micron films. Not only does the use of thick film capillary column provide excellent resolution, but it also has low flow rates that provide improved sensitivity. In fact, the improved sensitivity is about ten times better due to the very sharp peaks and improved resolving power.

To be clear, packed columns may also be used but the peaks are wider and the detection limits may require a considerably larger sample on the order of about 5-10 cc.

The PLOT column and the capillary column are available from various scientific equipment suppliers known to those skilled in the art. For the capillary or PLOT column, $O_2$ will be separated from the $MH_3$ gas so the sparger containing the aqueous sample does not have to be purged. In addition, the method of the present invention does not need a water trap or chiller when the optional precolumn (discussed later) is used.

For those measurements where a low parts-per-trillion level is needed, a sample is passed through an optional cation exchange column to collect the sample. The sample is then desorbed with a salt solution where the sample is now concentrated by a factor of 10. In one example, about 250 cc of 1 ppb sample is collected and then desorbed with 10 cc of 0.1 M sodium chloride solution. In another example, the sample is desorbed with about 25 cc of 0.1 M sodium nitrate solution.

Using the method of the present invention, directly injecting 1 cc of the substrate of the ionic species (e.g., the metal hydride) is sufficient to detect low or sub parts-per-billion levels.

Because many metals, non-metals and metalloids form hydrides and the corresponding metal hydrides have ionization potentials in the range of about 8-12 eV, the method of the present invention is capable of measuring various species including, but not limited to, arsenic, antimony, cadmium, lead, iron, chromium, germanium, indium, thorium, selenium, tellurium, bismuth, tin, and mercury, to name a few. Unlike arsenic, many of the other species have sensitivities much lower. The range is 10 to 100 times lower. For these species, a concentration step such as the use of the cation exchange column may be performed to detect low parts-per-billion levels.

Figure 1:
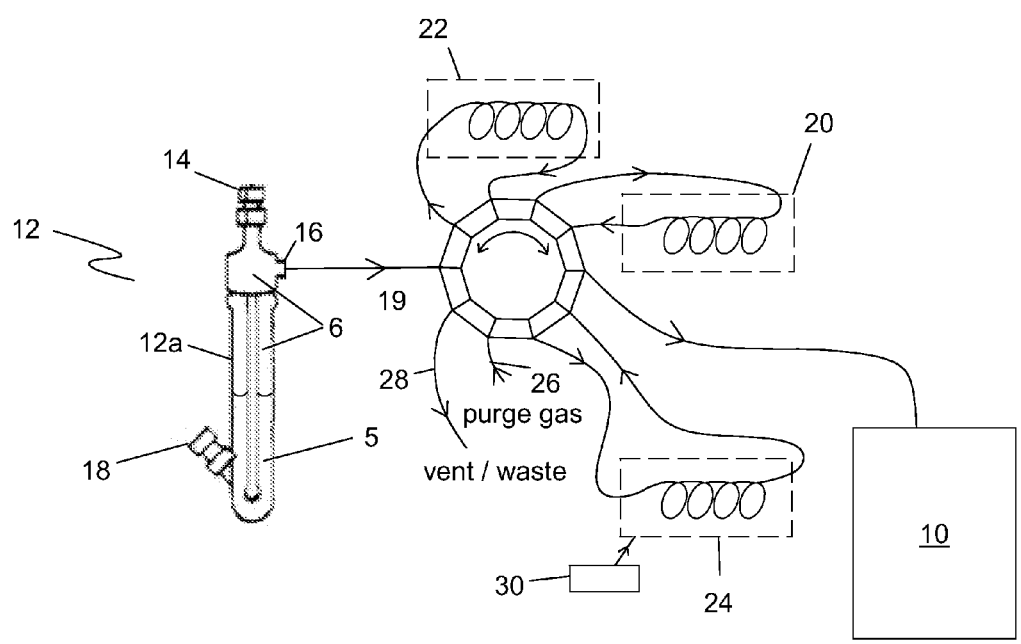
FIG. 1 is a schematic illustration showing the apparatus for performing the method of the present invention.

FIG. 1 schematically illustrates a system that uses the method of the present invention when using a detector system 10, which is either a PID detector or a GC equipped with a PID detector. This illustration includes a vessel 12 that is a sparger in this illustration, a gas input 14, a gas output 16 and port 18 for receiving a liquid sample 5 and/or a reducing agent and/or an oxidizing agent. The gas output 16 is connected to a 10-port valve 19 to facilitate sample handling. Also connected to valve 19 is a precolumn 22, an oxygen retaining column 20, an optional concentrator column 24 that is one of either a charcoal column or a gold film, a purging gas inlet 26, a vent/waste outlet 28, and the detector system 10. An optional cation exchange column described above and used for treating some samples having certain characteristics before adding the sample to the vessel 12 is not shown. Gas input 14 is the inlet for the nitrogen purge when used. Gas output 16 is for eluting the ionizable hydride species from the headspace 6 to the precolumn 22 and optionally through oxygen retaining column 20 when nitrogen gas is not used to purge vessel 12 of any air. The eluting ionizable hydride species is then injected into detector system 10 Optional concentrator column 24 is used as a concentrator of ionizable chemical gas species as the gas sample containing the ionizable chemical gas species is passed through concentrator column 24. Once an appropriate amount of the ionizable chemical gas species is retained in concentrator column 24, then concentrator column 24 is subjected to flash heating by a heat source 30 to release the ionizable chemical gas species. The ionizable chemical gas species is then injected into detector system 10. Concentrator column 24 is further explained below relating to the charcoal column for $MH_3$ concentration and the gold concentrator for increased sensitivity for mercury detection.

Detection of Various Species

The method of the present invention described above and illustrated in FIG. 1 was used to test known aqueous samples containing some of the listed species including arsenic, lead, iron, cadmium, and tin.

Unless disclosed in a particular example, each aqueous sample was placed in the sparging vessel and subjected to nitrogen purging for several minutes before the sodium borohydride reducing agent was added to the solution. The solution was stirred with a magnetic stirrer. The nitrogen purging removed most of the oxygen, which can quench the signal of the metal hydride. As described above in the method, the nitrogen purge was stopped but the stirring continued while the concentration of the metal hydride increased in the headspace of the sparger for a period of about 5 minutes after the addition of the reducing agent for levels greater than 50 ppb. For levels lower than 50 ppb, the time period of concentration was about 10 minutes to about 12 minutes. At the end of the predefined time period, the metal hydride gas generated in the sparging vessel was eluted to a GC/PID system.

Figure 2:
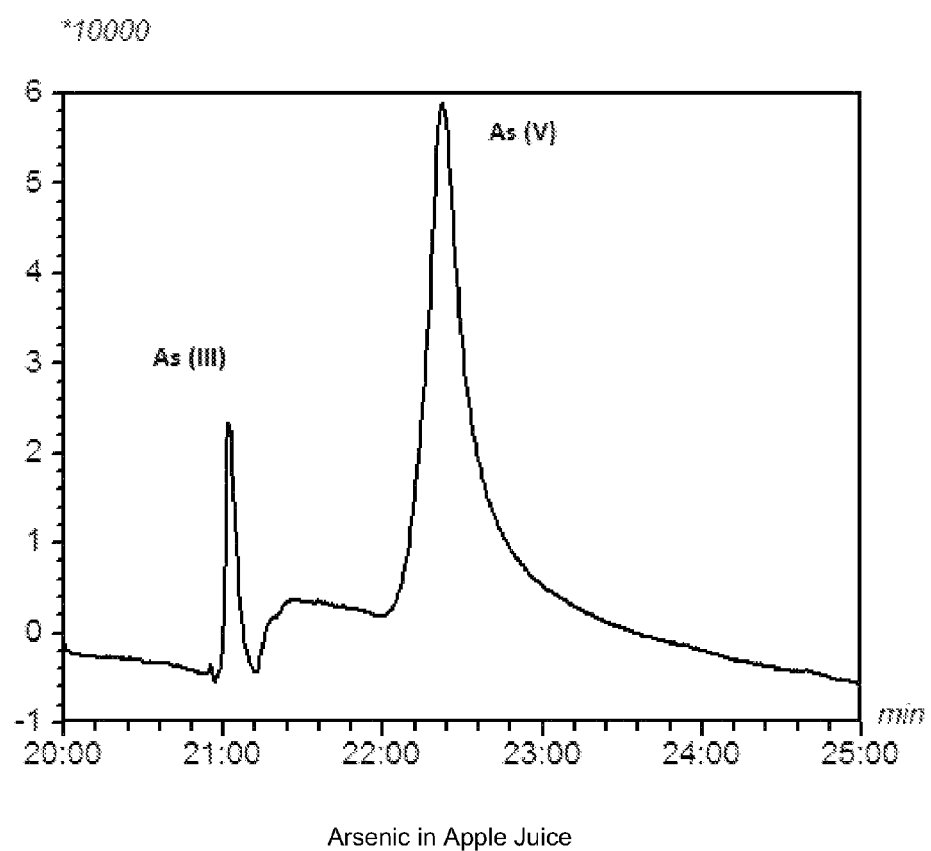
FIG. 2 is a trace of the signal output from the PID showing the PID response for arsenic using the method of the present invention.

FIG. 2 illustrates a graph of the counts measured by the PID detector for arsenic in apple juice. As can be seen in FIG. 2, the method of the present invention provides clear peaks for arsenic (III) and arsenic (V). The arsenic (III) has a concentration lower than the concentration for arsenic (V).

Figure 3A:
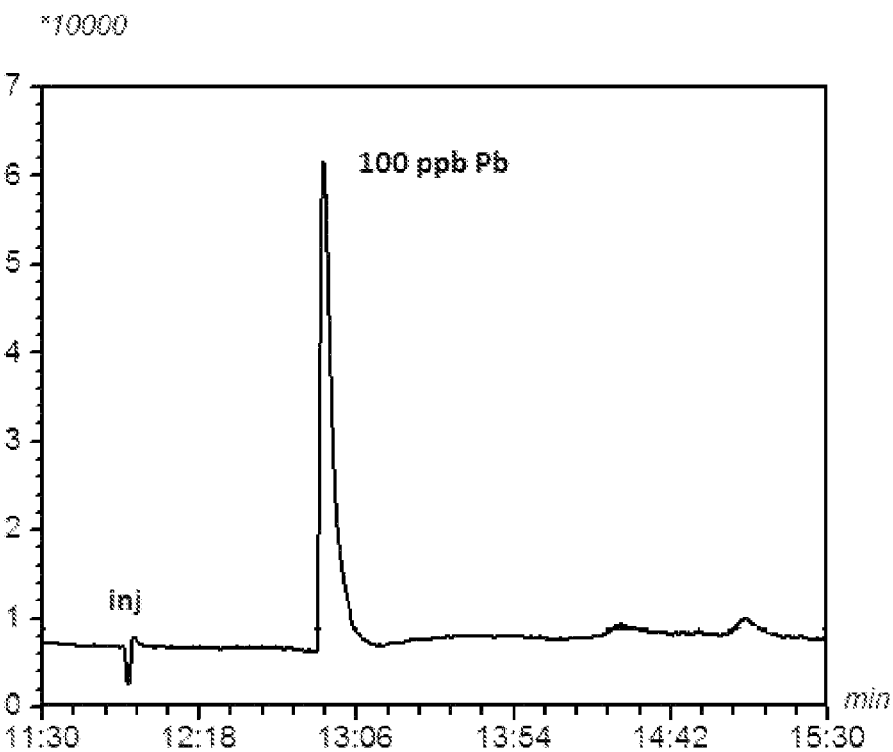
FIGS. 3A and 3B are traces of the signal output from the PID showing the PID response for lead using the method of the present invention.
Figure 3B:
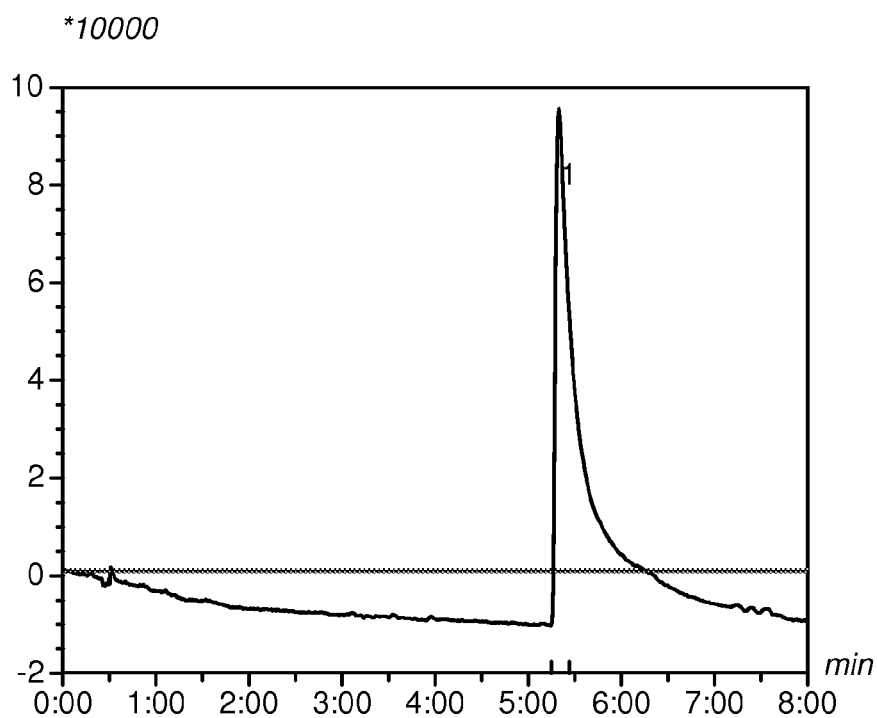

FIGS. 3A and 3B illustrate traces of the counts measured by PID detector for lead. The aqueous lead standard was prepared (with $H_2O_2$ added to convert $Pb^{+2}$ to $Pb^{+4}$) to provide a solution having about 100 ppb lead for each test. As shown in the FIG. 3A graph, the injection of the gas sample eluted from the sparging vessel was injected at about the 12 minute mark and the 100 ppb lead peak occurred about a minute later.

Unlike the method for the test in FIG. 3A, the test illustrated in FIG. 3B was run with no column, no drying agent, no stirrer, and the nitrogen purging was run for about 2.5 minutes to about 3 minutes and stopped 1 minute after addition of the sodium borohydride reducing agent. As shown in FIG. 3B, the lead peak is substantially similar to the lead peak shown in FIG. 3A. Except for the fact that lead sensitivity is one-tenth the sensitivity of arsenic, this experiment illustrates that inclusion of a stirring mechanism is optional with respect to the results obtained and the only difference is the wait time post nitrogen purging required before eluting the gas sample to the PID detector.

Figure 4:
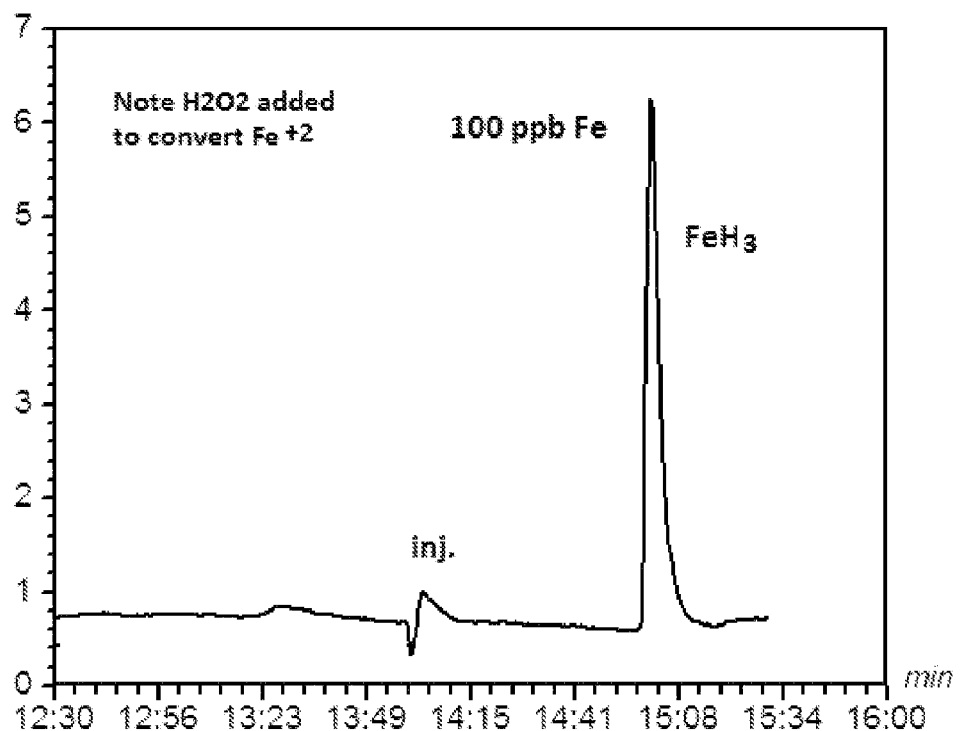
FIG. 4 is a trace of the signal output from the PID showing the PID response for iron using the method of the present invention with $H_2O_2$.

FIG. 4. Illustrates a trace of the counts measured by PID detector for iron. The iron standard was prepared to provide a solution having about 100 ppb. In this case, an oxidizing agent (e.g., hydrogen peroxide) was added to the sample to convert the $Fe^{+2}$ to $Fe^{+3}$. The graph indicates that a well-defined peak of 100 ppb iron was evidenced about 1 minute after injection.

Figure 5:
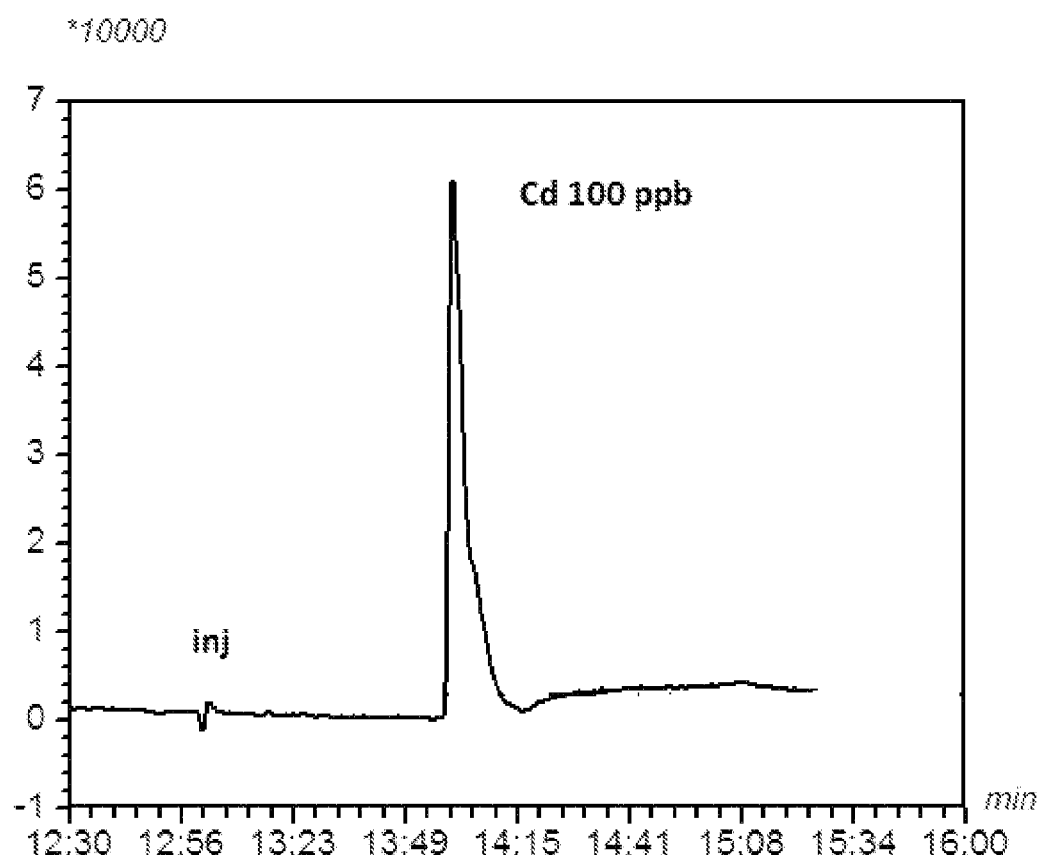
FIG. 5 is a trace of the signal output from the PID showing the PID response for cadmium using the method of the present invention.

Turning now to FIG. 5, there is illustrated a trace of the counts measured by PID detector for cadmium. The cadmium standard was prepared to provide a solution having about 100 ppb. The trace indicates that a well-defined peak of 100 ppb cadmium was evidenced a little over 1 minute after injection.

Figure 6:
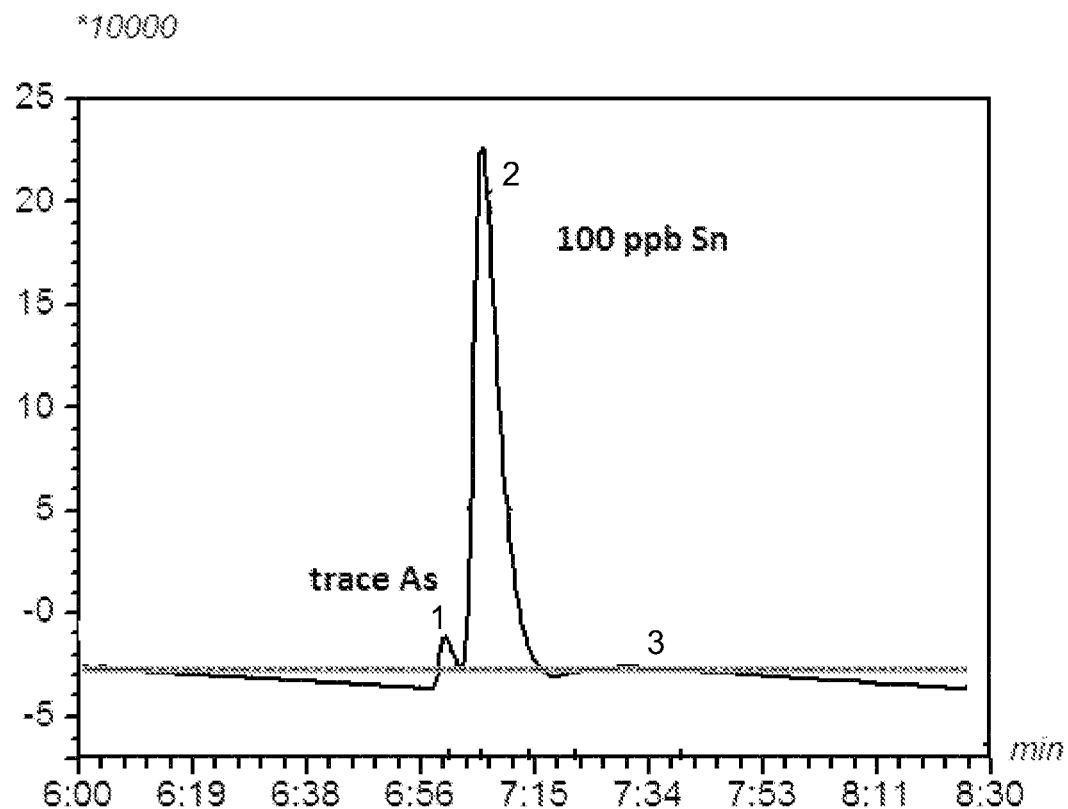
FIG. 6 is a trace of the signal output from the PID showing the PID response for tin using the method of the present invention.

FIG. 6 illustrates a trace of the counts measured by PID detector for tin. The tin standard was prepared to provide a solution having about 100 ppb. The trace indicates that a well-defined peak of 100 ppb tin after a small peak of trace arsenic was evidenced after injection.

Effect of Nitrogen Purging

Figure 7A:
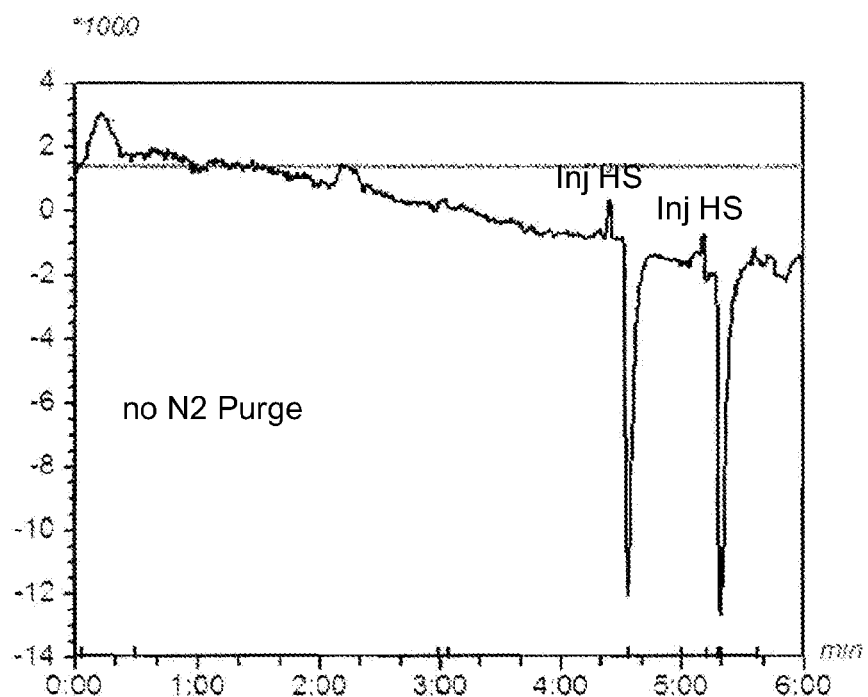
FIGS. 7A and 7B are traces of the signal output from the PID showing the effect of nitrogen purging on the PID response for arsenic using the method of the present invention.
Figure 7B:
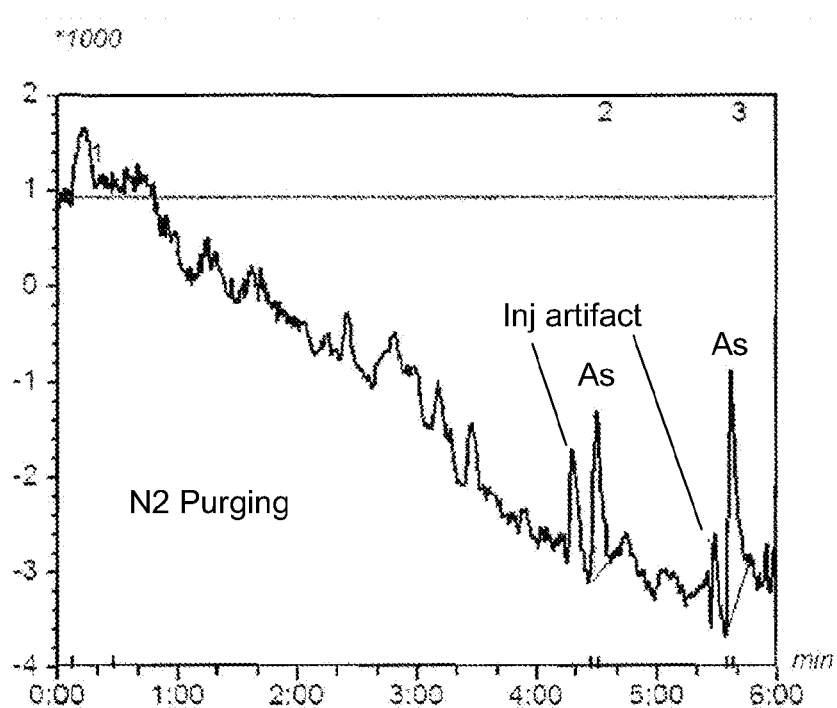

FIGS. 7A and 7B illustrate traces of the counts measured by PID detector for arsenic with and without nitrogen purging of the system for low ppb levels of arsenic. The samples were eluted through a packed column to remove the water in order to test the need for nitrogen purging the system of oxygen for low ppb level arsenic measurements. FIG. 7A represents no nitrogen purging. FIG. 7B represents nitrogen purging for 2-3 minutes. Because arsine ($AsH_3$) is a non-retained compound by the packed column along with oxygen (which quenches the PID response), FIGS. 7A and 7B show the effect on low ppb level of arsenic. As can be seen from the traces, when no nitrogen purging is performed, arsenic is completely masked. With nitrogen purging, the arsenic peak appears.

Sensitivity of PID

Figure 8A:
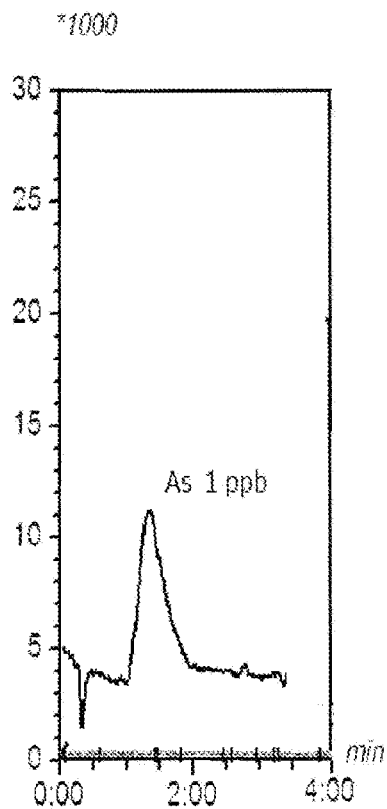
FIGS. 8A, 8B and 8C are traces of the signal output from the PID showing the PID response for three levels of arsenic using the method of the present invention.
Figure 8B:
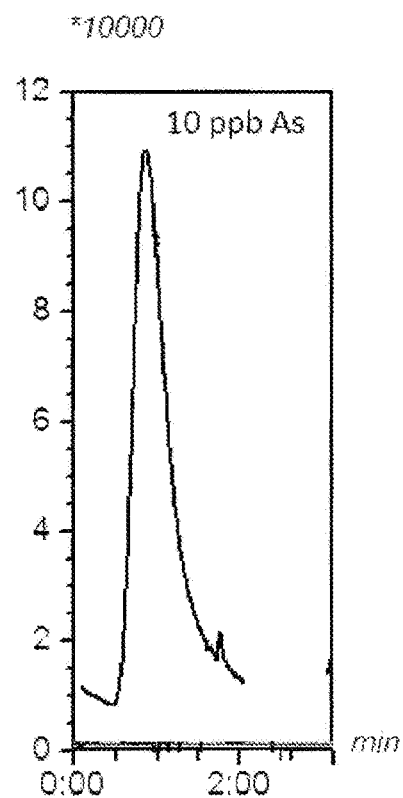
Figure 8C:
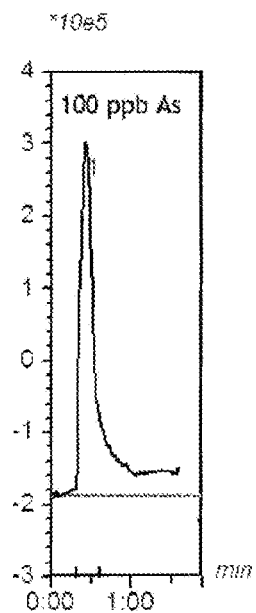

FIGS. 8A, 8B and 8C illustrate traces of the counts measured by PID detector for arsenic showing the sensitivity of PID to measure low levels of arsenic. FIG. 8A illustrates a trace for an aqueous sample containing 1 ppb of arsenic. FIG. 8B illustrates a trace for an aqueous sample containing 10 ppb of arsenic. FIG. 8C illustrates a trace for an aqueous sample containing 100 ppb of arsenic.

Figure 9:
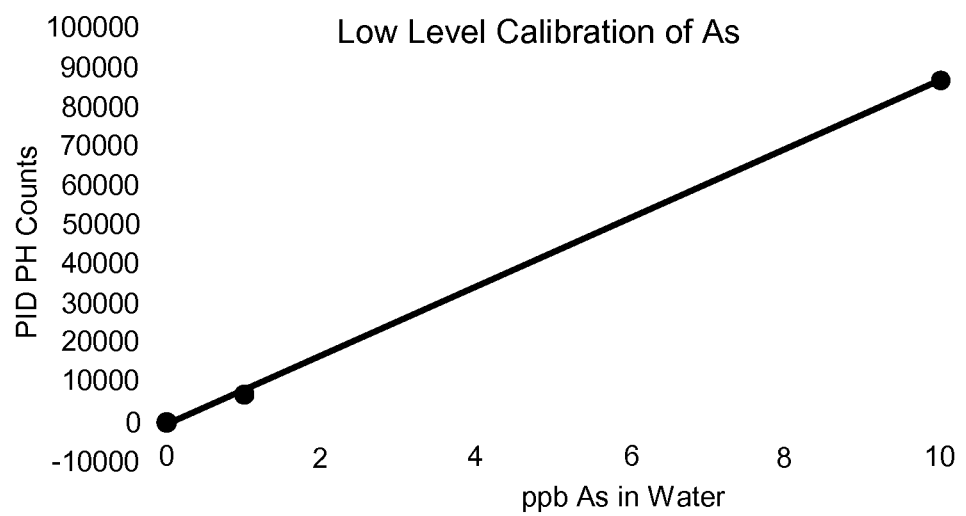
FIG. 9 is a graph showing a low level calibration curve of the PID response for arsenic using the method of the present invention.

FIG. 9 illustrates a plot/graph of the counts measured by PID for 1 ppb and 10 ppb of arsenic. The graph indicates that it is a linear correlation of the measured counts and, thus, a reliable method for determining low ppb levels of arsenic.

Figure 10A:
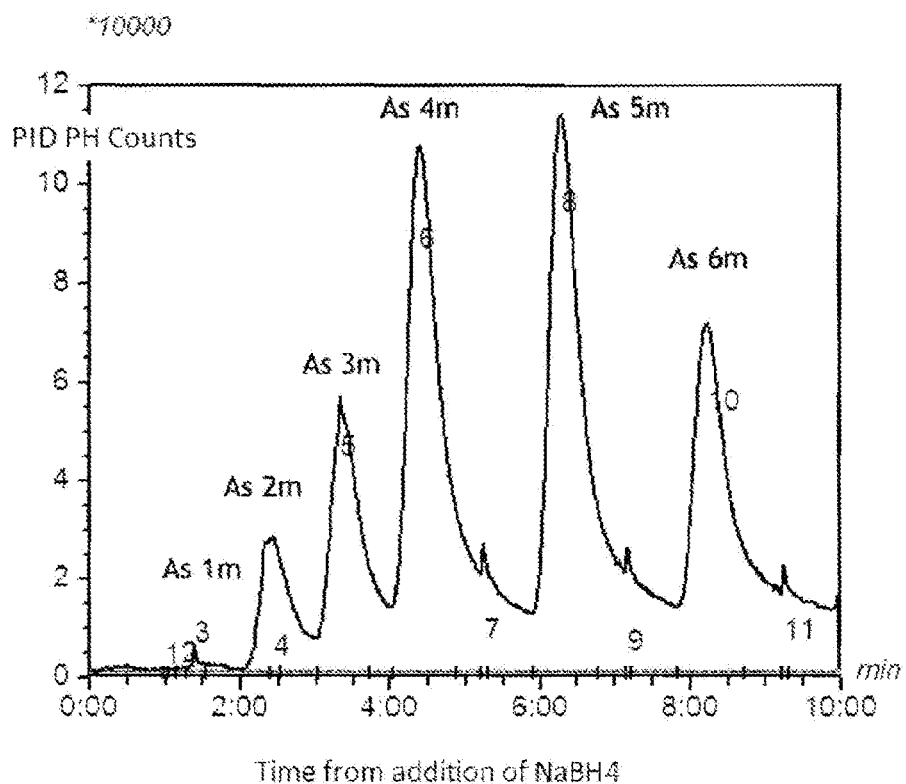
FIG. 10A is a trace of the signal output from the PID showing the PID response for arsenic using the method of the present invention while sampling at 1 minute intervals.
Figure 10B:
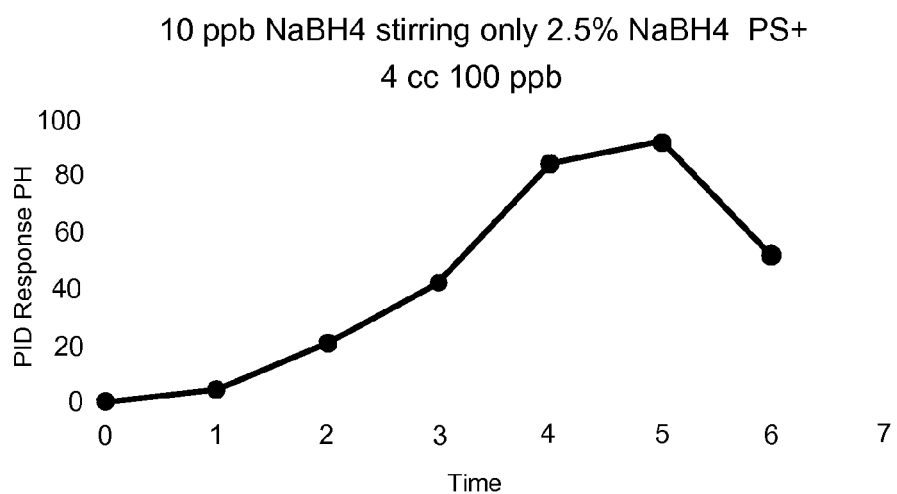
FIG. 10B is a graph showing a curve of the trace values shown in FIG. 10A.

FIGS. 10A and 10B illustrate a trace and a graph, respectively, of the counts measured by PID of an aqueous sample containing 10 ppb arsenic in water. The sample was purged for 2-3 minutes with nitrogen and then the reducing agent (sodium borohydride) was added and the nitrogen purge was stopped while stirring was continued. A 1 cc gas sample was injected every minute. As can be seen from FIG. 10A, the maximum value occurs between 4-6 minutes so multiple injections can be made. FIG. 10B is a plot/graph of the peak height values. The level of arsenic that is necessary to measure as published by the EPA is 10 ppm in drinking water and 10 ppb in apple juice (by the FDA). Thus, a 1 ppb measurement is necessary for any analytical method for detection of arsenic.

Effect of Incorporating a Column on Low PPB Levels

Figure 11:
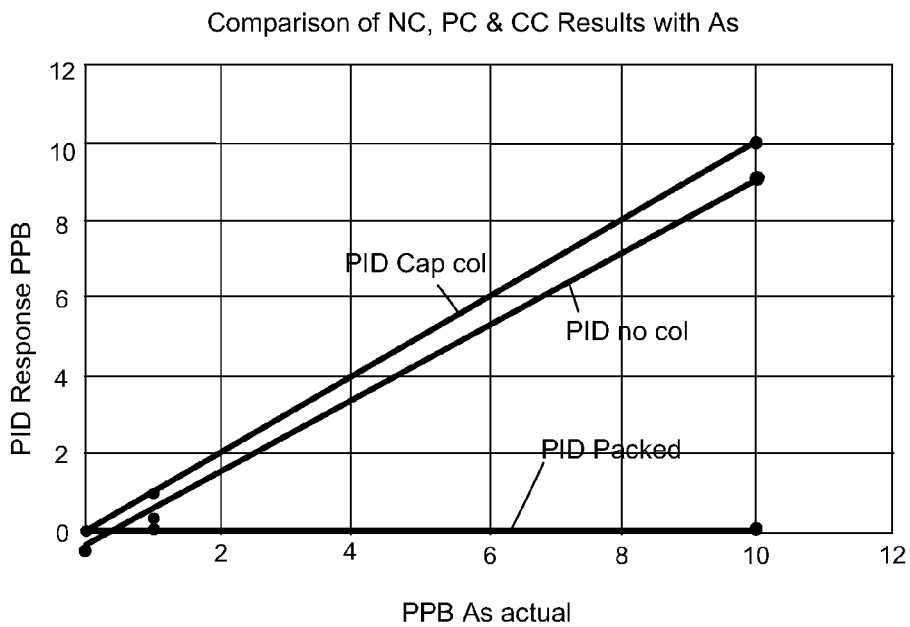
FIG. 11 is a graph showing the effect using a packed or capillary column on the PID response for arsenic.

FIG. 11 illustrates a graph comparing the results using arsenic as the species of interest showing the effect the type of column has on the PID response. The x-axis is the actual ppb of arsenic in the measured sample and the y-axis is the PID measured ppb of arsenic. It is apparent from the test data that the capillary column provides the best results at low ppb levels. When no column was incorporated in the test and no nitrogen purge, the signal was lowered by greater than ten percent (10%). It is noteworthy that at the 1 ppb level where nitrogen purging was used to remove oxygen, the value obtained was 0.35 ppb instead of the expected 1 ppb. This was caused by water vapor and represents a reduction in sensitivity of greater than 80%. It was also found that, when a packed column is used (6 ft.×⅛ in. (188.9 cm×0.32 cm) column packed with Tenax® GS), arsine ($AsH_3$) is an unretained compound and elutes very close to the air peak indicating that nitrogen purging for several minutes to remove oxygen is required to prevent quenching of the signal.

Figure 12:
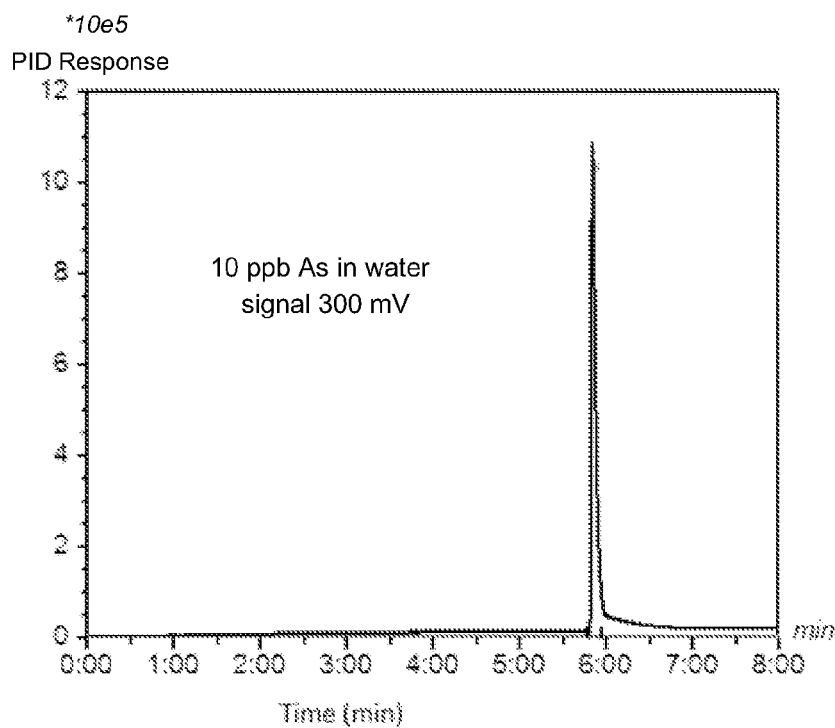
FIG. 12 is a trace of the signal output from the PID showing the PID response for arsenic using the method of the present invention and incorporating an optional capillary column.

FIG. 12 illustrates a trace showing the PID response for a 10 ppb As aqueous sample using a capillary column. As evidenced by the trace, the signal peak is sharp and pronounced.

Effect of an Oxidizing Agent

Figure 13:
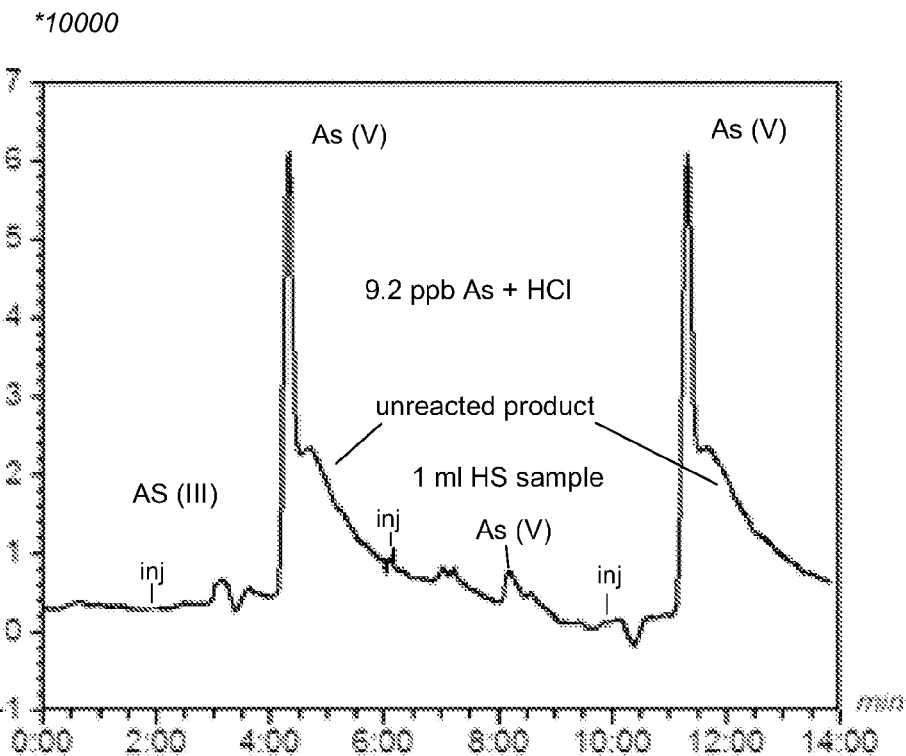
FIG. 13 is a trace of the signal output from the PID showing the PID response for arsenic using the method of the present invention.
Figure 14:
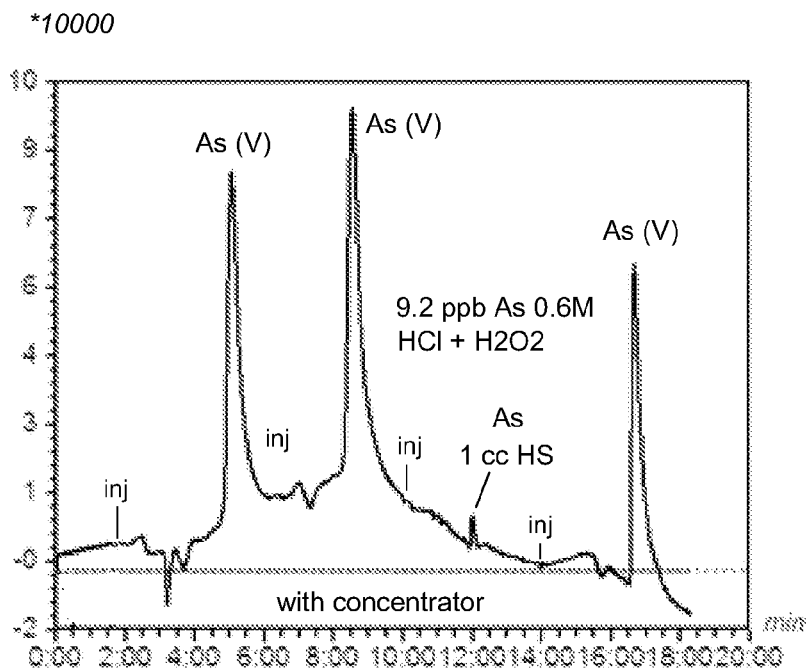
FIG. 14 is a trace of the signal output from the PID showing the PID response for arsenic using the method of the present invention where an oxidizing agent is added to the sample for hydride generation.
Figure 15:
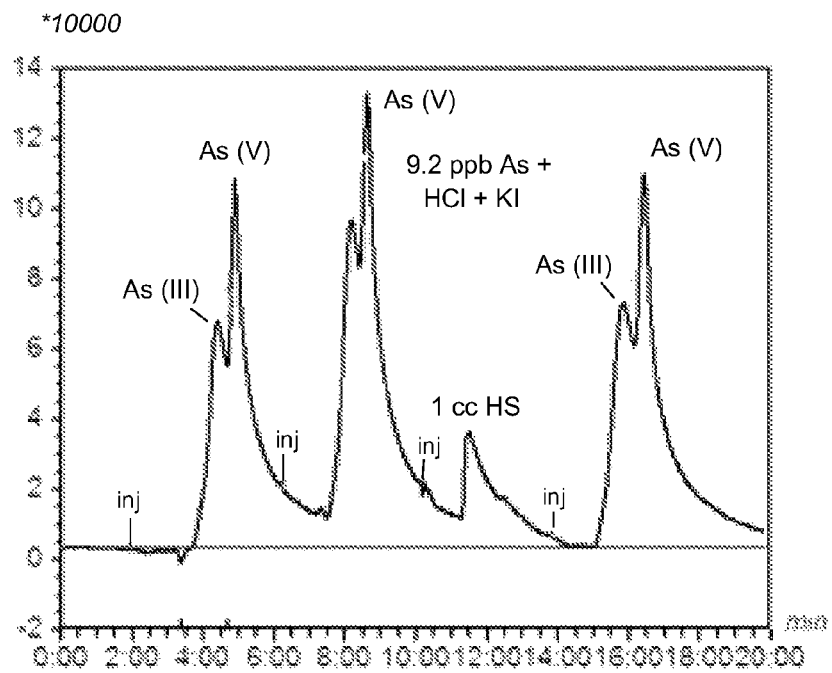
FIG. 15 is a trace of the signal output from the PID showing the PID response for arsenic using the method of the present invention but including KI reducing agent in the sample for hydride generation.

FIGS. 13-15 illustrate traces showing the effect of incorporating an oxidizing agent in an aqueous sample of low level arsenic. In these experiments, a 9.2 ppb aqueous arsenic sample in 0.6M HCl was prepared. One (1) cc of sodium borohydride reducing agent was added to the sample to start the reduction. This is typical hydride generation procedure known to the skilled artisan. For these experiments, a concentrator/trap was used. Specifically, the concentrator/trap used was third column 24 containing activated charcoal. After collection, the 6" (15.24 cm) trap (i.e. third column 24) was heated to 150° C. for about 1 to about 2 minutes and the sample was injected through a 10 port valve to remove the $AsH_3$ and conduct it to the detection system.

FIG. 13 illustrates a trace of the arsenic sample after being desorbed from the trap. As seen in the trace, at 1 minute after injection, a small peak of As(III) and a large peak of As(V) was obtained. The As(V) peak has a broad area after the peak, which is believed to be unreacted product. It is noted that this is not seen at higher levels due to kinetics, which slow considerably at low concentrations.

FIG. 14 illustrates a trace of the arsenic sample where an oxidizing agent was added to the aqueous sample. In this case, the oxidizing agent was hydrogen peroxide ($H_2O_2$). A 1 ml of 3% $H_2O_2$ has added to the aqueous sample to convert As(III) to As(V) and to promote the reaction of the unreacted product As(V) seen in FIG. 13. A comparison to FIG. 13 shows that the As(V) peak in FIG. 14 does not have the long tail observed in FIG. 13 and peak height (PH) and peak area (PA) have increased by greater than 30 percent (30%). The conventional method of treatment is opposite, which uses potassium iodide (KI) to reduce As(V) to As(III). This is illustrated in FIG. 15.

Turning now to FIG. 15, there is illustrated a trace of the conventional method of treatment that uses potassium iodide (KI) to reduce As(V) to As(III). In this conventional method, 1 cc of 2% KI is added to the aqueous sample. As shown in FIG. 15, the peak for As(III) is enhanced but there is still As(V) being eluted. This continues to occur even after 14 minutes.

From a comparison of FIGS. 14 and 15, it appears that the addition of an oxidizing agent to oxidize As(III) to As(V) gives a cleaner signal and is a better procedure than the addition of KI, which reduces As(V) to As(III). However, the PID with a capillary column will detect and separate both $As^{+3}$ and $As^{+5}$.

Multiple Species Detection

Figure 16:
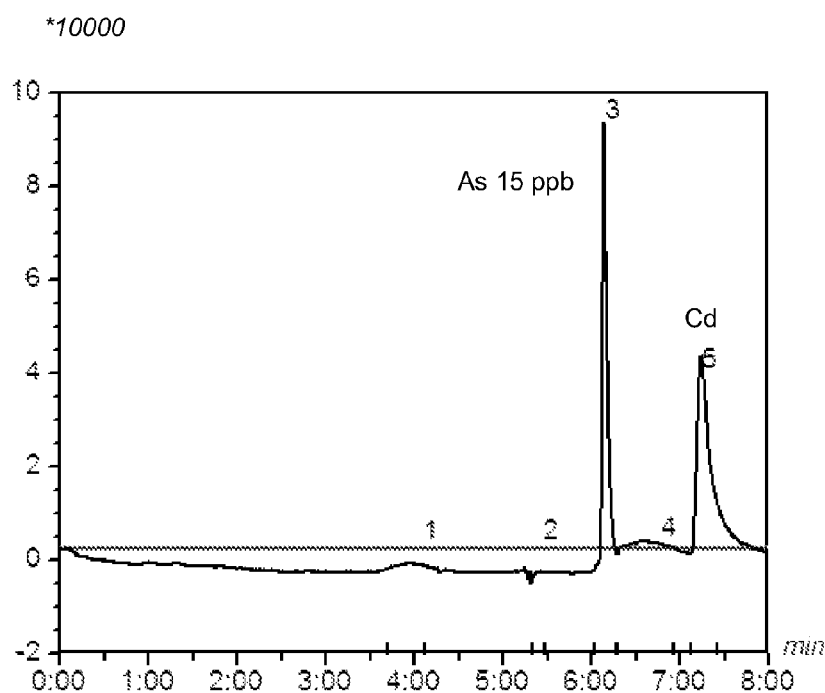
FIG. 16 is a trace of the signal output from the PID showing the PID response for multiple ionic species using the method of the present invention.

FIG. 16 illustrates the effectiveness of the present invention for the detection of multiple species in an aqueous sample. In this particular experiment, a sample was prepared that included 15 ppb As (arsenic) and 60 ppb Cd (cadmium). The procedure included using a thick film capillary column with the method described earlier. Specifically, the sample was prepared by mixing 10 cc of Cd, 5 cc of As plus 5 cc of deionized water. A nitrogen purge was used per the method of the present invention before adding the reducing agent $NaBH_4$. The PID flow was 20 cc per minute. As seen in FIG. 16, the arsenic peak and the cadmium peak are relatively sharp and the signals are clearly separated showing that multiple metals are detectable using the method of the present invention The advantages of the present invention include (1) continuous nitrogen purging is not required, but could still be used (2) a cold trap to remove water is not required when a precolumn is used, (3) a liquid nitrogen trap/concentrator for collecting the metal hydride is not required, (4) a nitrogen purge is used for a short period of time to remove oxygen to prevent signal quenching, (5) only a 1 cc gas sample of the headspace is required to obtain usable results, and (6) using PID to measure multiple species is more cost effective than any other conventional method.

Precolumn for $MH_x$

In another embodiment of the present invention, it has been found that water and other organics may be better separated from the metal hydride sample without the use of a water trap as shown in FIG. 17 of the prior art. The 8-port switch is replaced with a 10-port switch and a six inch column that we call a "precolumn" is added to the sample path prior to injection into the GC/PID. The precolumn is packed with a porous polymer like HayeSep N. Because the $MH_x$ has a similar retention to air when passed through the precolumn, the $MH_3$ will go through the precolumn very quickly. Water, on the other hand, is retained within the precolumn along with most organics for a longer period of time. It was determined that if a short injection time of about 10 seconds to about 14 seconds is used, the $MH_3$ and air would be separated from the water and organics. The water and organics can then be purged from the precolumn eliminating these interferences.

The following table shows various retention times of compounds for HayeSep N, Q, R, S, and T.

TABLE 1

Relative retention times (in minutes) for HayeSep N, Q, R, S, and T Ethane = 1.00; Column: 6' × ⅛" SS at 65° C. Flow: He 30 cc/min

| Compound | N | Q | R | S | T |
|---|---|---|---|---|---|
| Hydrogen | 0.19 | .143 | 0.17 | .19 | .21 |
| Air | 0.23 | .186 | 0.2 | .21 | .25 |
| Nitric oxide | 0.25 | .217 | 0.21 | .23 | .33 |
| Methane | 0.30 | .256 | 0.28 | 0.3 | .35 |
| Carbon dioxide | 0.71 | 0.45 | 0.50 | 0.52 | 0.85 |
| Nitrous oxide | 0.80 | 0.57 | 0.59 | 0.59 | — |
| Ethylene | 0.83 | 0.74 | 0.78 | 0.78 | 0.9 |
| Acetylene | 1.41 | 0.74 | 1.0 | 0.87 | 2.11 |
| Ethane | 1.0 | 1.0 | 1.0 | 1.0 | 1.0 |
| Water | 10.1 | 1.45 | 6.80 | 4.12 | 19.1 |
| Hydrogen sulfide | 2.1 | 1.40 | 1.73 | 1.87 | 2.88 |
| Hydrogen cyanide | 19.3 | 2.31 | 15.6 | 8.26 | 28.8 |
| Carbonyl sulfide | 2.82 | 2.33 | 2.46 | 2.63 | 3.4 |
| Sulfur dioxide | 12.0 | 3.05 | 9.78 | 17.8 | 19.0 |
| Propylene | 4.66 | 3.20 | 3.45 | 3.65 | 4.91 |
| Propane | 4.66 | 3.67 | 3.88 | 4.1 | 4.63 |
| Propadiene | 6.50 | 4.12 | 4.39 | 4.7 | 7.55 |
| Methylacetylene | 9.5 | 4.12 | 4.84 | 5.14 | 11.3 |
| Methyl chloride | 7.43 | 3.93 | 4.67 | 4.92 | 9.2 |
| Vinyl chloride | 14.9 | 6.04 | 9.04 | 9.7 | 17.3 |
| Ethylene oxide | 17.7 | 6.06 | 8.78 | 9.7 | 23.3 |
| Ethyl chloride | 35.0 | 12.25 | 19.3 | 20.7 | 43.2 |
| Carbon disulfide | — | 32.4 | — | — | 40.7 |

As shown in Table 1, air and $MH_x$ are gases with a relatively short retention time (0.23 minutes) while water has a relative retention time of ten (10) minutes or forty (40) times longer than air and $MH_3$. Even ethylene has a retention time four (4) times longer than air so with a short injection time even ethylene would not get through to the analytical column.

Charcoal Column for $MH_x$ Concentration

It was further discovered that, instead of using (1) a nitrogen trap or (2) stopping $N_2$ purging of the sample to allow generation of sufficient $MH_3$ for detection by the GC/PID, ppb levels of $MH_3$ from a hydride generator is retained in a six inch (6") (15.24 cm) charcoal column and illustrated in FIG. 1 as a third column 24. The process involves passing the gas sample through the precolumn 22, the optional oxygen retaining column 20 for the same reasons as previously discussed before venting the nitrogen containing $MH_x$ into the charcoal column for about five to about 10 minutes to collect all of the $MH_3$. Once all of the MH3 is removed from the vessel 12, the charcoal column 24 is heated to 150° C. for about 1 to about 2 minutes to drive the metal out of the charcoal column and into an inlet port of the 10-port valve and then onto the detector system 10. It was found that, for $AsH_3$, it could take 10 minutes or more to deplete the $AsH_3$ from the solution. This means a many fold increase in the sample for the GC/PID.

Static Headspace Instead of a Sparging Vessel

It was further discovered that the oxygen peak in a sample run could be substantially eliminated by modifying the sample reaction vessel. In this embodiment, a sparging vessel is replaced with a VOA vial. The VOA vial is a 40 ml VOA vial with a cover and a septum typically made of a polytetrafluoroethylene (PTFE) such as the material sold under the trademark Teflon®. Unlike the sparging vessel that has an air-containing headspace, the VOA vial is used to avoid any air in the headspace. This is accomplished by adding 1 ml of concentrated hydrochloric acid (HCl) and a PTFE stirring bar to the vial. The vial is then filled to the brim with sample. The septum and the cover are then attached to the vial. A syringe is used to penetrate the septum and about 10 ml of the liquid in the vial is removed. The remaining liquid is stirred for several minutes to mix the sample and HCl before adding 1 ml of a reducing agent such as 4% sodium borahydride ($NaBH_4$) solution. The sample solution with the reducing agent is stirred for another 5-10 minutes. A 1 ml sample is removed and injected into the GC/PID. One advantage of this embodiment is that it is simpler and does not require much equipment. Another advantage is that the $O_2$ peak is nearly eliminated because there is no headspace that has to be purged since the concentration of $O_2$ in water is only about 20 ppm.

Increased Sensitivity for Mercury Detection/Determination

During the development of the present invention, it was discovered that the PID method for mercury is made more sensitive and specific using a preconcentration process. When mercury is to be determined in a water sample, the mercury sample that contains the mercury salt is added to the vessel 12 along with the sodium borohydride ($NaBH_4$). Unlike other species that form a hydride, mercury is released as free mercury in gas form. The gas sample containing the mercury is then passed by a gold film. Any mercury in the gas sample reacts with the gold at room temperature to form a Au/Hg amalgam. Water and other organics that were no removed previously are now removed by purging with $N_2$ gas for several minutes. After purging, the gold film containing the Au/Hg amalgam is heated rapidly (i.e. about 25-30 seconds) to 500° C. to decompose the amalgam and free the Hg, which is detected by the PID.

Detection of Mercury in Air

The technique of using third column 24 can also be used for detecting Hg in air. Because the Hg is already in a gaseous state, the air is directly passed by a gold film. With enough sample, this method can detect 10 ppt (parts per trillion) of Hg specifically. The process involves passing about 40-50 liters of air through a gold film with $N_2$ gas for several minutes to remove water and other. The gold film is then subjected to flash heating (i.e. about 25-30 seconds) up to 500° C. to decompose the amalgam and free the Hg, which is detected by the PID.

Concentrator Apparatus for Mercury

Figure 18:
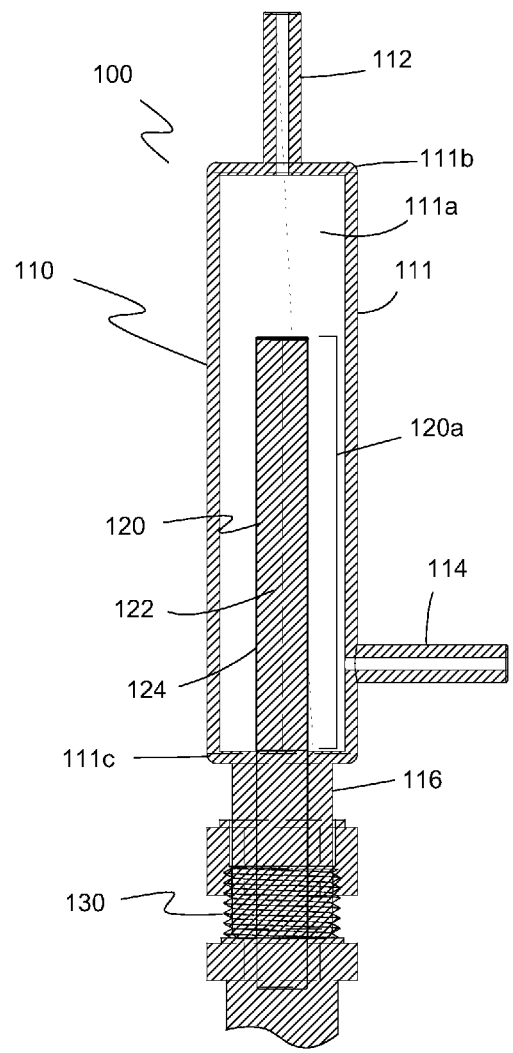
FIG. 18 is a cross-sectional view of the embodiment of the concentrator shown in FIG. 17.

For mercury detection, a novel concentrator has been devised. Turning now to FIGS. 17 and 18, there is illustrated one embodiment of the concentrator for mercury. The concentrator 100 includes a quartz assembly 110, a mercury concentrator element 120 and a heater 130. Quartz assembly 110 includes a tubular quartz body 111 that defines an internal volume 111a. A gas inlet 112 is connected to a first body end 111b and a gas outlet is transversely to quartz body 111. There is also a heater end 116 that is connected to quartz body 111 at a second body end 111c, which is opposite the gas inlet 112. A substantial first element portion 120a of mercury concentrator element 120 is disposed within quartz body 111. Either a gas sample or a purging gas flows through gas inlet 112, into internal volume 111a and around first element portion 120a before exiting out gas outlet 114.

Figure 19:
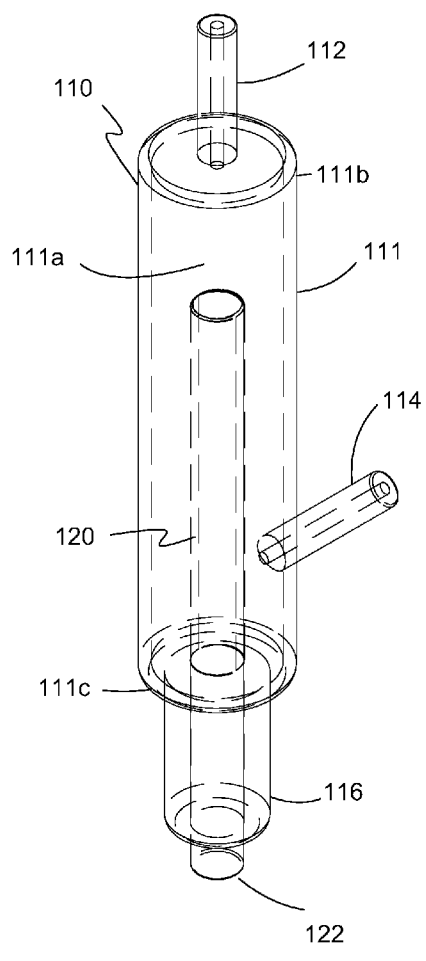
FIG. 19 is a perspective view of the concentrator without heater attachment shown in FIG. 17.
Figure 20:
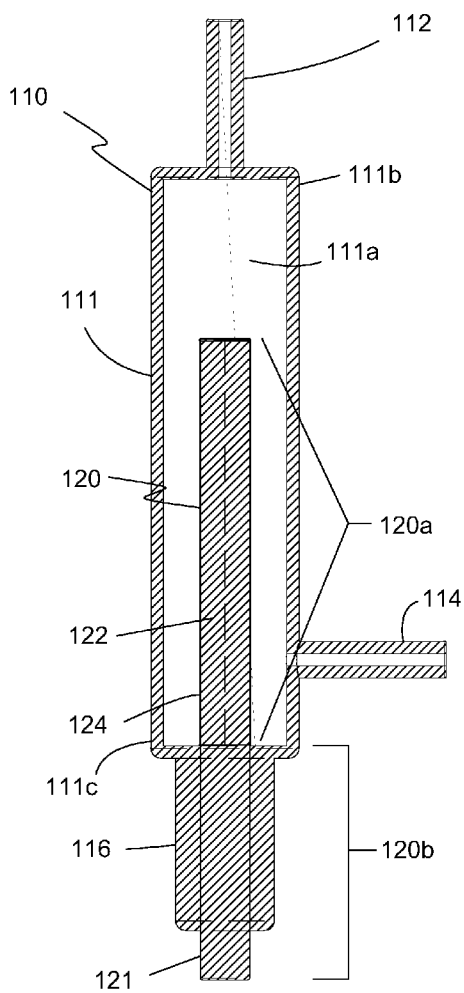
FIG. 20 is a cross-sectional view of the embodiment of the concentrator shown in FIG. 19.

Turning now to FIGS. 19 and 20, there is illustrated the mercury concentrator assembly 100 that includes quartz assembly 110 and mercury concentrator element 120. Quartz assembly 110 has tubular quartz body 111, gas inlet 112, gas outlet 114, and heater end 116. Mercury concentrator element 120 includes an element core 122 in the shape of a rod, a gold layer/coating 124 over element core 122. Concentrator element also has first element portion 120a and a second element portion 120b. Element core 122 is typically made of stainless steel. First element portion 120a is that portion of concentrator element 120 that is disposed within internal volume 111a. Second element portion 120b is that portion that is disposed within heater end 116 and includes an end element portion 121 that extends out of quartz body 111 through heater end 116. Heater end 116 is sealed around concentrator element 120. A gold film 124 is coated/deposited over at least first element portion 120a. It is the gold film 124 that reacts with the mercury gas to form an amalgam. It is understood that gold film 124 may be deposited over the entire surface of element core 122.

In the illustrated embodiment, the quartz body 111 is about 4.5 inches (about 11.4 cm) long. The gas inlet 112 and the gas outlet 114 are ¼" (0.635 cm) diameter and the heater end 116 is about 0.5" (1.27 cm) diameter. First element portion 120a is about 3.5" (8.9 cm) long. The element core 122 is made of 304 stainless steel, polished and then plated with gold. The heater 130 is attached to heater end 116 using a stainless steel reducing adapter and the ferrule used in the fitting is made of graphite. The heater 130 is a 300 watt heater, which incorporates a thermocouple. The heater operates using 115 VAC and is capable of heating to 500° C. in about 30 seconds. It is understood that the dimensions may be modified to accomplish the desired result and the above described dimensions are not to be construed as limiting.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method for detecting a chemical species in an aqueous ionic sample by a detector system, the method comprising:
providing, in a vessel, an acidic sample containing an ionic chemical species to be measured wherein a substrate of the species to be formed is ionizable by radiant energy provided by a photoionization detector in the detector system and wherein the vessel has a headspace above the acidic sample;

adding a preselected reducing agent to the aqueous sample and forming an ionizable chemical gas species in the aqueous sample whereby the ionizable chemical gas species evolves out of the aqueous sample and into the headspace forming a gas sample;

conducting the gas sample containing the ionizable chemical gas species from the headspace of the vessel out of the vessel and through a precolumn wherein the precolumn retains water and other organics of the gas sample in the precolumn while passing the gas sample containing the ionizable chemical gas species through the precolumn; and conducting the gas sample containing the ionizable chemical gas species from the precolumn into one of (1) a photoionization detector or a gas chromatograph having a photoionization detector if the headspace is purged with nitrogen gas prior to performing the adding step, or, (2) an oxygen-retaining column before conducting the gas sample into a photoionization detector or a gas chromatograph having a photoionization detector if the headspace contains oxygen before the adding step is performed, wherein the method is performed without using a liquid nitrogen cold trap.

2. The method of claim 1 further comprising providing an oxygen retaining column selected from the group consisting of a packed column, a PLOT column, and a capillary column to receive the gas sample before being ionized by radiant energy.

3. The method of claim 2 wherein the capillary column is a thick film capillary column.

4. The method of claim 1 wherein the sample providing step includes selecting an ionic sample having one or more of a metal, nonmetal or metalloid that forms a hydride.

5. The method of claim 1 wherein the sample providing step includes selecting a sample having one or more ionic species selected from the tellurium, bismuth, tin, mercury, hydrogen sulfide, hydrogen selenide, and hydrogen telluride.

6. The method of claim 1 further comprising selecting an aqueous sample having an ionic species wherein a substrate of the ionic species has an ionization potential in the range of 8-12 eV.

7. The method of claim 1 wherein the adding step includes selecting sodium borohydride as the reducing agent.

8. The method of claim 1 wherein the adding step further includes adding an oxidizing agent.

9. The method of claim 8 further comprising selecting hydrogen peroxide as the oxidizing agent.

10. The method of claim 1 further comprising passing a predefined quantity of the aqueous ionic sample containing the ionic species through a cation exchange column and desorbing the ionic species from the cation exchange column with a smaller predefined quantity of a salt solution before placing the aqueous ionic sample in the vessel.

11. The method of claim 1 further comprising passing the gas sample through a concentrator column to accumulate the ionizable chemical gas species in the concentrator column before moving the gas sample into the photoionization detector or a gas chromatograph having a photoionization detector and then quickly heating the concentrator column to a predefined temperature to release the ionizable chemical gas species followed by conducting the released ionizable chemical gas species into the photoionization detector or a gas chromatograph having a photoionization detector.

12. The method of claim 11 further comprising selecting a concentrator column that contains activated charcoal if the ionizable chemical gas species is an ionizable gas hydride substrate of the chemical species.

13. The method of claim 12 wherein the quickly heating step includes heating to a temperature of 150° C. in 1 to 2 minutes if the concentrator column contains activated charcoal.

14. The method of claim 11 further comprising selecting a concentrator column that contains gold film if the ionizable chemical gas species is mercury.

15. The method of claim 14 wherein the quickly heating step includes heating to a temperature of 500° C. in 25 to 30 seconds if the concentrator column contains gold film.

16. The method of claim 1 further comprising selecting a vessel that is a sparging vessel.

17. The method of claim 1 further comprising selecting a vessel that is a VOA vial with a septum, filling the vial so no headspace exists above the acidic sample and removing a predefined quantity of the sample from the vessel through the septum creating a headspace.

18. The method of claim 1 wherein the gas sample, after passing through the precolumn, is passed through an oxygen-retaining column that is a capillary column if the ionic chemical gas species is arsenic to separate $As^{+3}$ and $As^{+5}$ not withstanding the contents of the headspace.

* * * * *